(12) United States Patent
Inukai et al.

(10) Patent No.: US 7,393,327 B2
(45) Date of Patent: Jul. 1, 2008

(54) BLOOD PRESSURE MONITORING APPARATUS

(75) Inventors: Hidekatsu Inukai, Nagoya (JP); Toru Oka, Ichinomiya (JP)

(73) Assignee: Fukuda Denshi Co., Ltd., Tokyo (JP)

( * ) Notice: Subject to any disclaimer, the term of this patent is extended or adjusted under 35 U.S.C. 154(b) by 0 days.

(21) Appl. No.: 11/475,938

(22) Filed: Jun. 28, 2006

(65) Prior Publication Data

US 2007/0016086 A1    Jan. 18, 2007

(30) Foreign Application Priority Data

Jun. 29, 2005 (JP) ............................. 2005-190469
Jun. 29, 2005 (JP) ............................. 2005-190470

(51) Int. Cl.
*A61B 5/02* (2006.01)

(52) U.S. Cl. ...................... 600/485; 600/500; 600/483; 600/490

(58) Field of Classification Search .................. 600/481, 600/483, 485, 486, 488, 490–504
See application file for complete search history.

(56) References Cited

FOREIGN PATENT DOCUMENTS

JP         10-066681         3/1998

OTHER PUBLICATIONS

Iketani et al., "Photoplethysmogram (Accelerated Pulse Wave) for Evaluating Degree of Arteriosclerosis by Hypertension", Blood Pressure, vol. 10, No. 6, 2003, pp. 54-60 (English translation attached).

*Primary Examiner*—Charles A. Marmor, II
*Assistant Examiner*—Navin Natnithithadha
(74) *Attorney, Agent, or Firm*—Drinker Biddle & Reath LLP

(57) ABSTRACT

In blood pressure monitoring apparatus which continuously estimates and monitors blood pressure by using the pulse wave propagation time, blood pressure fluctuation can be accurately estimated. If both blood pressure estimated from the pulse wave propagation time and a waveform parameter obtained from the accelerated pulse wave have abnormal values, it is determined that the blood pressure is truly fluctuating, and blood pressure measurement by another method, e.g., blood pressure measurement using a cuff is performed.

25 Claims, 5 Drawing Sheets

BLOOD PRESSURE MONITORING APPARATUS

CLAIM OF PRIORITY

This application claims priority from Japanese Patent Application Nos. 2005-190496 and 2005-190470, both filed on Jun. 29, 2005, which are hereby incorporated by reference herein.

FIELD OF THE INVENTION

The present invention relates to blood pressure monitoring apparatus for noninvasively and continuously monitoring blood pressure.

BACKGROUND OF THE INVENTION

In an operating room, ICU, or the like, it is sometimes necessary to continuously monitor the blood pressure of a patient. As a conventional technique of noninvasively and continuously monitoring the blood pressure, blood pressure estimation based on the pulse wave propagation time is known.

This technique uses the fact that the time (pulse wave propagation time) required for a pulse wave to propagate between two points in a living body or the pulse wave propagation velocity obtained by dividing the blood vessel length between the two points by the pulse wave propagation time has a correlation with the blood pressure. For example, the pulse wave propagation time is continuously measured and applied to an expression having a precalibrated coefficient, thereby continuously calculating and monitoring an estimated blood pressure (e.g., Japanese Patent Laid-Open No. 10-66681).

To measure the pulse wave propagation time, however, pulse waves must be measured in different locations, so the measurement requires a long time. Also, it is sometimes difficult to attach sensors or cuffs for measuring pulse waves to two locations. As described in Japanese Patent Laid-Open No. 10-66681, therefore, a general approach is to calculate the pulse wave propagation time by using an electrocardiogram (ECG) normally measured by a biological information monitoring apparatus and a pulse wave measured in one predetermined location (e.g., a fingertip) of a living body.

Unfortunately, the use of an ECG in the calculation of the pulse wave propagation time has a problem of the measurement accuracy. That is, an ECG is a signal which represents not a pulse wave but the electrical state change of the heart. There is a time difference (preejection period) between the timing at which the electrical state change occurs and the timing at which the heart actually contracts to generate a pulse wave. Accordingly, the pulse wave propagation time calculated by using the observation timing of the feature point of an ECG as a starting point contains an error caused by the preejection period.

If the preelection period is constant, this error is easy to correct. However, the preejection period changes from one person to another, and can change occasionally even in the same person. Therefore, an improvement of the accuracy by correction is limited.

Blood pressure monitoring apparatus normally performs control such that if blood pressure continuously measured on the basis of the pulse wave propagation time is abnormal, more accurate blood pressure measurement is performed by using a cuff or the like, and an alarm is output if an abnormal value is detected by this measurement.

Blood pressure measurement using a cuff is established as a method of noninvasively measuring the blood pressure, and effective to automatically obtain a well reliable blood pressure. However, this method requires avascularization, so the frequent use of the method is undesirable because the load on a patient increases. Therefore, accurate determination of the need for cuff blood pressure measurement is important not only to perform an appropriate therapy but also to reduce the load on a patient.

To increase the determination accuracy as described above, it is also important to increase the accuracy of the estimated blood pressure based on the pulse wave propagation time calculated from an ECG and a pulse wave observed at one point.

SUMMARY OF THE INVENTION

The present invention has been made in consideration of the problems of the prior art as described above, and has as its object to make it possible to more accurately determine the necessity of high-accuracy blood pressure measurement, in blood pressure monitoring apparatus which continuously estimates blood pressure on the basis of the pulse wave propagation time, and performs more accurate blood pressure measurement where necessary.

It is another object of the present invention to increase the accuracy of an estimated blood pressure in blood pressure monitoring apparatus which continuously estimates blood pressure on the basis of the pulse wave propagation time.

According to one aspect of the present invention, there is provided a blood pressure monitoring apparatus comprising: blood pressure measuring unit adapted to measure blood pressure in response to blood pressure measurement designation; pulse wave acquiring unit adapted to acquire a pulse wave in a predetermined location of a living body; pulse wave propagation time calculating unit adapted to calculate a pulse wave propagation time from the pulse wave, and one of an electrocardiogram and a pulse wave acquired from a location different from the predetermined location; estimated blood pressure calculating unit adapted to calculate an estimated blood pressure on the basis of the pulse wave propagation time; accelerated pulse wave calculating unit adapted to calculate an accelerated pulse wave from the pulse wave; waveform parameter calculating unit adapted to calculate a predetermined waveform parameter from a waveform contained in the accelerated pulse wave; and control unit adapted to provide the blood pressure measurement designation to the blood pressure measuring unit to cause the blood pressure measuring unit to measure blood pressure, if both the estimated blood pressure and the predetermined waveform parameter are abnormal.

According to another aspect of the present invention, there is provided a blood pressure monitoring apparatus comprising: blood pressure measuring unit adapted to measure blood pressure by a predetermined method; pulse wave acquiring unit adapted to acquire a pulse wave in a predetermined location of a living body; pulse wave propagation time calculating unit adapted to calculate a pulse wave propagation time from the pulse wave, and one of an electrocardiogram and a pulse wave acquired from a location different from the predetermined location; estimated blood pressure calculating unit adapted to calculate an estimated blood pressure by applying the pulse wave propagation time to a predetermined expression; accelerated pulse wave calculating unit adapted to calculate an accelerated pulse wave from the pulse wave; waveform parameter calculating unit adapted to calculate a predetermined waveform parameter from a waveform contained in the accelerated pulse wave; and calibrating unit adapted to calibrate the expression by using a value measured by the blood pressure measuring unit, wherein if a fluctuation amount of the waveform parameter exceeds a predetermined amount, the calibrating unit performs the calibration after correcting a calibration amount which is applied when the fluctuation amount of the waveform parameter does not exceed the predetermined amount.

In the present invention having the above arrangements, the necessity of blood pressure measurement by another method is determined by considering: the waveform parameter, which is obtained from the accelerated pulse wave and reflecting the functional state of the blood vessel, is taken into consideration as well as the continuous estimated blood pressure, which is based on the pulse wave propagation time calculated from an ECG and a pulse wave observed at one point. Therefore, the determination accuracy can be increased.

Also, according to the present invention, the waveform parameter obtained from the accelerated pulse wave is taken into consideration in the calculation of the continuous estimated blood pressure based on the pulse wave propagation time calculated from an ECG and a pulse wave measured at one point. Accordingly, the accuracy of the estimated blood pressure can be increased.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENT

A preferred embodiment of the present invention will now be described in detail in accordance with the accompanying drawings.

Figure 1:
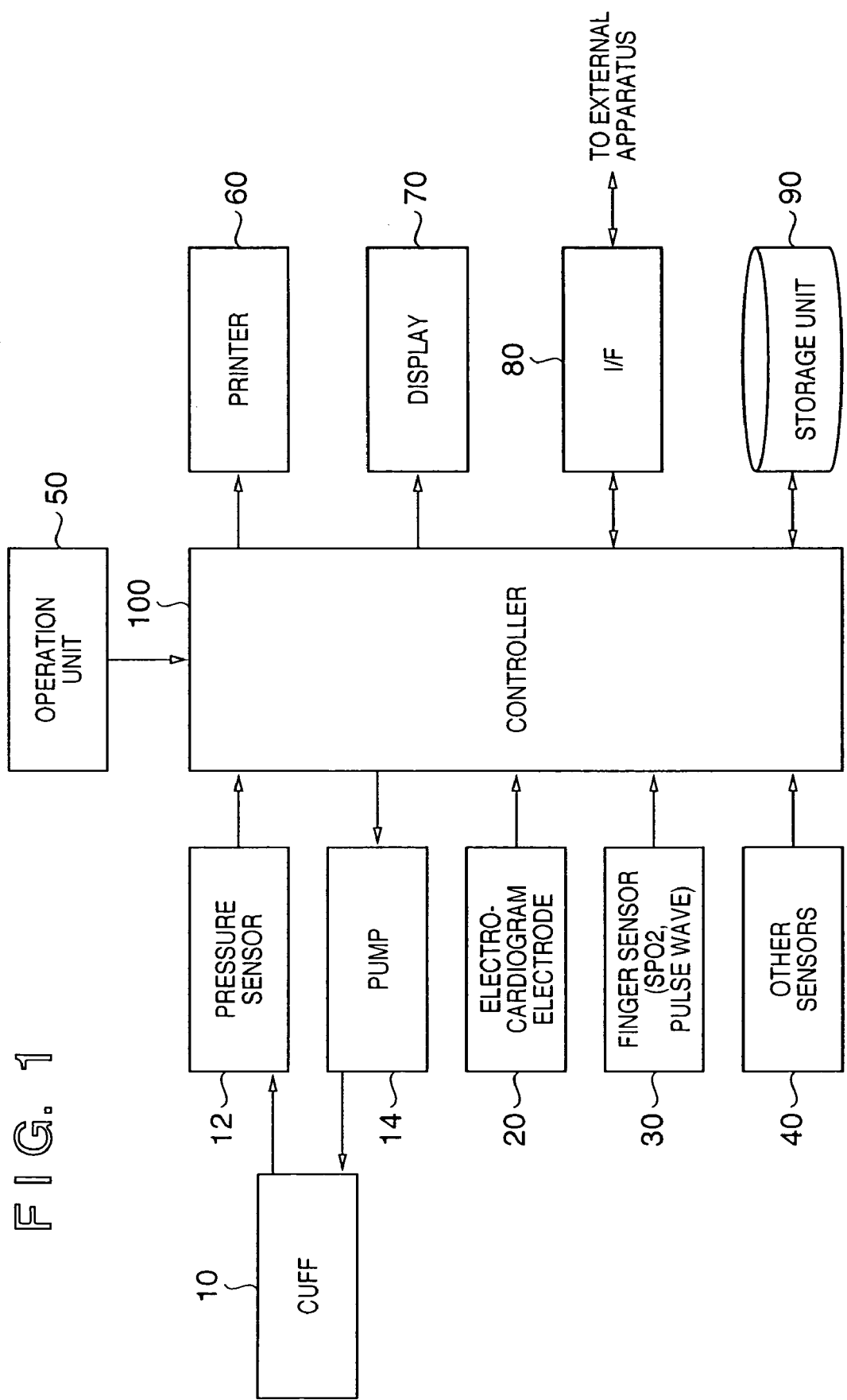
FIG. 1 is a block diagram showing an example of the arrangement of a biological information monitoring apparatus as blood pressure monitoring apparatus according to an embodiment of the present invention.

FIG. 1 is a block diagram showing an example of the functional arrangement of a biological information monitoring apparatus as blood pressure monitoring apparatus according to the embodiment of the present invention.

Referring to FIG. 1, a cuff 10 has a band-like form, and incorporates a rubber pouch which expands and contracts by pumping of a pump 14. The cuff 10 is normally attached to one of the limbs, typically the upper arm of a patient. A pressure sensor 12 senses a change in pressure applied to the gas filled in the internal rubber pouch of the cuff 10, converts the pressure signal into an electrical signal, and outputs the electrical signal to a controller 100.

An electrocardiogram (ECG) electrode 20 comprising a plurality of electrodes is attached to a predetermined position of the chest of a patient, and outputs an induced waveform as an ECG signal to the controller 100. A finger sensor 30 is a so-called pulse oximeter which optically senses and outputs an oxygen saturation degree (SPO2) and plethysmograph to the controller 100. The absorbance of hemoglobin changes in accordance with whether hemoglobin combines with oxygen, and also changes in accordance with the wavelength of light. On the basis of these facts, the finger sensor 30 generally measures the oxygen saturation degree by using two wavelengths, i.e., red light and infrared light. Also, since the AC component of transmitted light or reflected light changes in accordance with the blood flow volume, this AC component is detected as a photoplethysmograph (PTG).

Other sensors 40 sense other biological information such as the respiration and body temperature of a patient, and one or more sensors are connected to the controller 100 as needed. The other sensors 40 are not directly related to the blood pressure monitoring operation of this embodiment, so no further explanation thereof will be made.

An operation unit 50 is a man-machine interface by which the user (measurer) inputs various settings and information concerning a patient and provides instructions to the biological information monitoring apparatus. The operation unit 50 is generally constructed by appropriately combining a keyboard, a mouse, buttons, switches, dials, a touch panel, and the like.

A printer 60 and display 70 are representative output devices, and visually output the state of the apparatus, measurement results, and the like. An external interface (I/F) 80 is typically a network interface, serial interface (e.g., a USB or IEEE1394), modem, or the like, and communicates with an external apparatus which is connected invasively or across a network.

A storage unit 90 is typically a hard disk drive, and records programs for controlling the operation of the biological information monitoring apparatus, various data, measurement results, personal information of patients, and the like. The storage unit 90 may also include at least one other type of storage device, e.g., a device which reads and writes a writable removable medium such as a memory card or an optical disk.

The controller 100 controls the operation of the whole biological information monitoring apparatus. The controller 100 has, e.g., a CPU and RAM, and controls the individual units by loading the control programs stored in the storage unit 90 into the RAM and executing the loaded programs by the CPU, thereby implementing processes including the blood pressure monitoring operation (to be described later) of the biological information monitoring apparatus. Note that not all the processes need be executed using software by the CPU. For example, signal processing such as A/D conversion and filtering of signals input from the various sensors may also be assigned to a DSP or dedicated hardware, thereby appropriately using another arrangement.

The blood pressure monitoring operation by the biological information monitoring apparatus of this embodiment will be explained below.

The biological information monitoring apparatus of this embodiment is similar to the prior art in that the pulse wave propagation velocity is continuously calculated by using an ECG and plethysmograph, and an estimated blood pressure is continuously calculated by using an expression having a precalibrated coefficient, and that the necessity of blood pressure measurement using a cuff is determined by using the estimated blood pressure.

In this embodiment, however, it is determined that blood pressure measurement using a cuff is necessary only when another condition is met in addition to the estimated blood pressure, thereby increasing the abnormality detection accuracy in continuous blood pressure monitoring. This embodiment is characterized in that the value of a parameter obtained from an accelerated pulse wave is used as the other condition.

Figure 2:
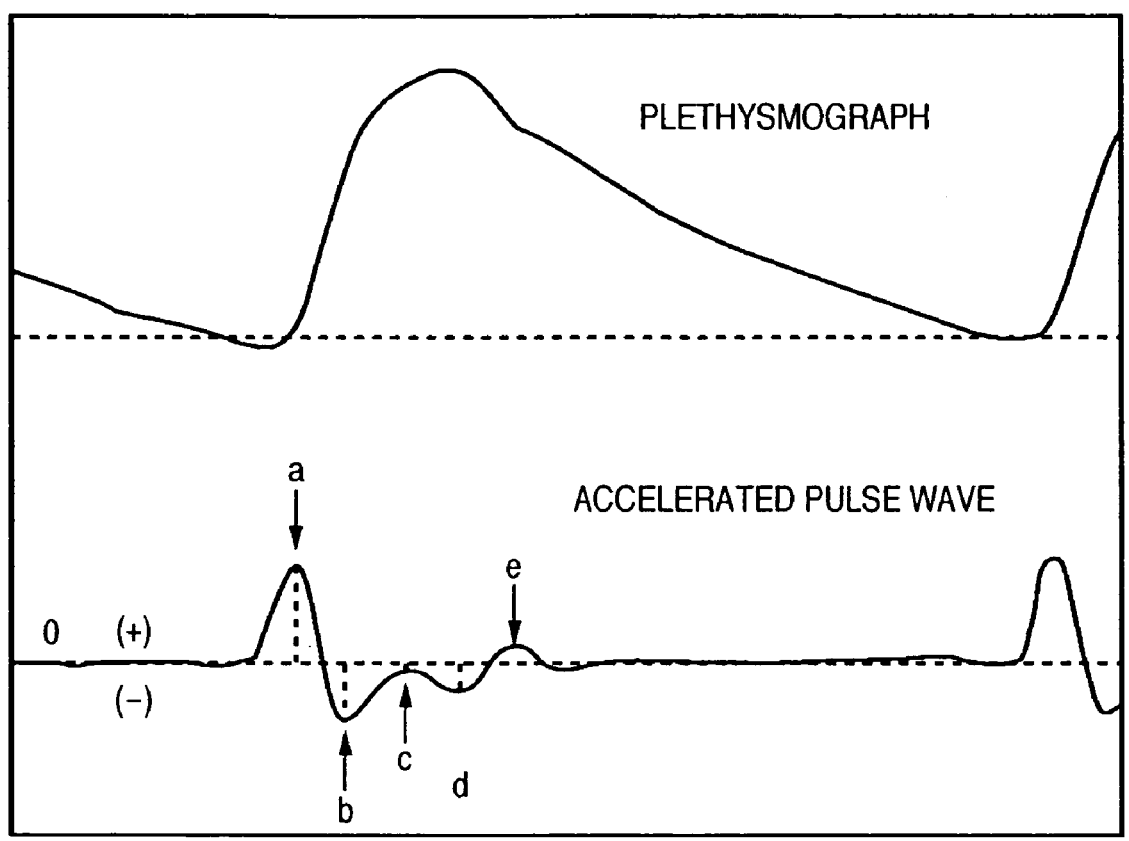
FIG. 2 is a graph showing examples of an original waveform and its accelerated pulse wave.

The accelerated pulse wave is obtained by calculating the second derivative of a pulse wave, and has characteristic waves from a-wave to e-wave as shown in FIG. 2. A-wave and b-wave represent presystolic components, c-wave and d-wave represent telesystolic components, and e-wave represents a diastolic component (e.g., Iketani et al., "Photoplethysmogram (Accelerated Pulse Wave) for Evaluating Degree of Arteriosclerosis by Hypertension", Blood Pressure, vol. 10, no. 6, 2003, pp. 54-60.

According to Iketani et al., the presystolic component reflects-a driving pressure wave generated by ejection of the blood when the heart contracts, and the telesystolic component is a re-elevated pressure wave generated when the driving pressure wave propagates to the periphery, and the returned reflected wave overlaps the driving pressure wave. Accordingly, it can be presumed that the presystolic component represents the state of the heart (center), and the telesystolic component represents the state of the periphery.

In this embodiment, therefore, the condition that at least one of the presystolic component or telesystolic component fluctuates by an amount exceeding a predetermined amount from the value of the presystolic component or telesystolic component obtained when the blood pressure was measured last time by using a cuff is used as the other condition described above. That is, it is possible to determine that the possibility that the blood pressure has actually fluctuated is higher when a change is found in the center or periphery in addition to the change in estimated blood pressure, than when only the estimated blood pressure fluctuates or only the change in the center or periphery is found.

Note that in this embodiment, a wave height ratio b/a of b-wave to a-wave is used as a parameter indicating the state of the center, and a wave height ratio d/a of d-wave to a-wave is used as a parameter indicating the state of the periphery. The ratios to the wave height of a-wave are herein used in order to compare the parameters obtained from an accelerated pulse wave when no calibration exists in a strict sense, and this is a kind of normalization.

Figure 3:
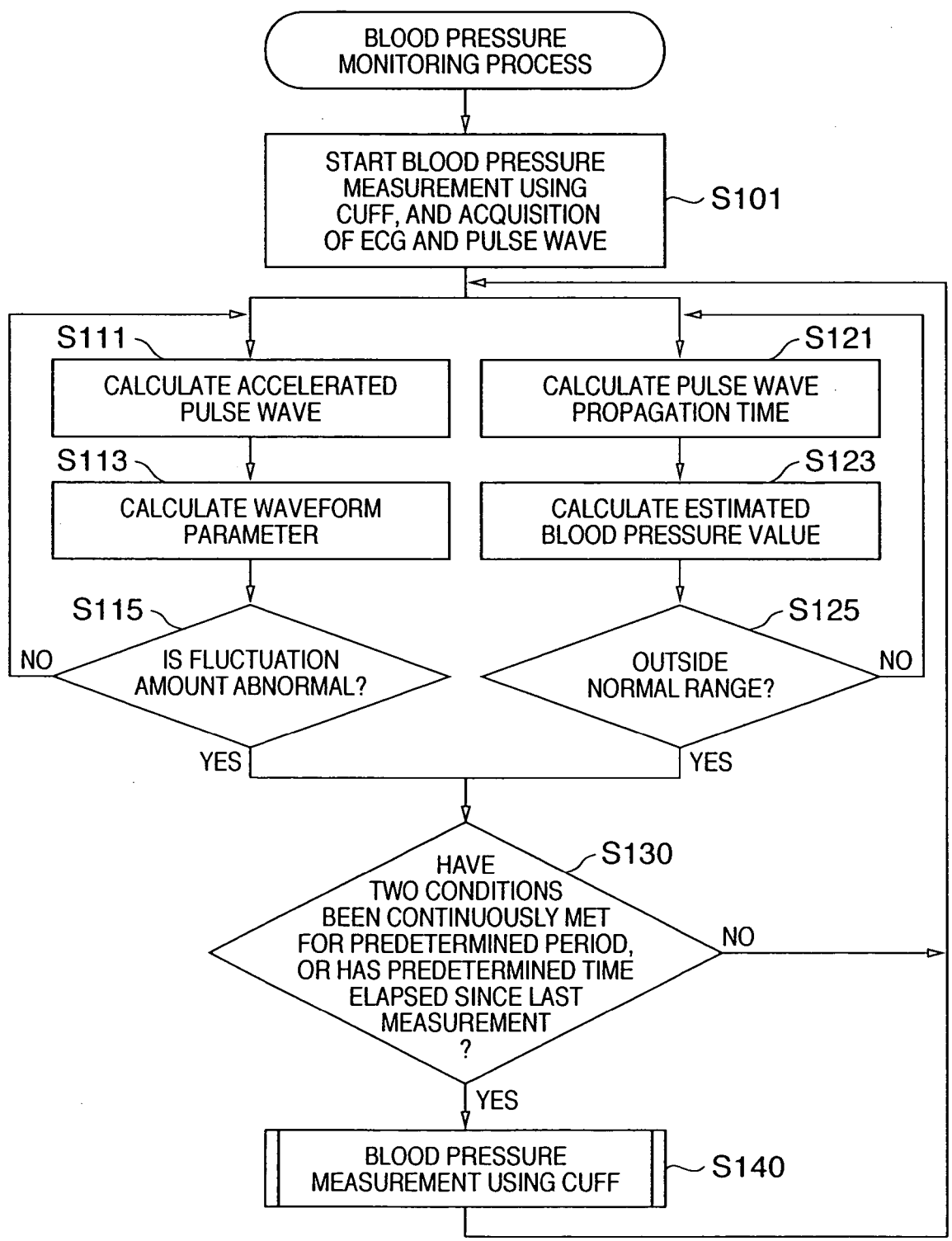
FIG. 3 is a flowchart explaining the blood pressure monitoring operation of the biological information monitoring apparatus according to the embodiment of the present invention.

On the basis of the above description, the blood pressure monitoring operation of the biological information monitoring apparatus according to this embodiment will be explained with reference to a flowchart shown in FIG. 3.

First, in step S101, the acquisition of an ECG and pulse wave is started. Also, as initialization, initial blood pressure measurement using a cuff is performed, and the initial values of an accelerated pulse wave parameter and estimated blood pressure are calculated by a method to be explained below, and stored in the storage unit 90. After that, the processing (steps S111 to S115) of the accelerated pulse wave and the process (steps S121 to S125) of estimating the blood pressure on the basis of the pulse wave propagation velocity are performed in parallel.

In step S111, the controller 100 calculates the accelerated pulse wave from the photoelectric plethysmograph from the finger sensor 30. In step S113, on the basis of a-wave to d-wave contained in one pulse of the accelerated pulse wave, parameters concerning the presystolic component and telesystolic component, i.e., the wave height ratios b/a and d/a in this embodiment, are obtained.

In step S115, the controller 100 calculates fluctuations from the obtained parameter values and values obtained in the last cuff blood pressure measurement, and determines whether the fluctuations are abnormal. For example, the controller 100 sets $$D1(\%)=1-\{b/a(\text{current})\}/\{b/a(\text{ref})\}\times 100$$

$$D2(\%)=1-\{d/a(\text{current})\}/\{d/a(\text{ref})\}\times 100$$

The controller 100 can check the presence/absence of abnormality by determining whether one, both, or a predetermined one of $$|D1|>Thb \quad (1a)$$

$$|D2|>Thd \quad (1b)$$

is satisfied. Since, however, b/a is a parameter indicating the state of the center, it is desirable to take account of at least the value of b/a. In step S115, the parameters as objects of abnormality determination, the expressions for abnormality determination, and the threshold values used are predetermined. However, these values and expressions need not be fixed but can be changed any time.

Note that in the above equations, (current) indicates a present calculated value, and (ref) indicates a reference calculated value obtained in the last cuff blood pressure measurement. Note also that the threshold values Thb and Thd indicating normal ranges can be either equal or individually set. In addition, the fluctuation need not be absolute values, and it is also possible to individually set the threshold value (upper limit) on the increasing side and the threshold value (lower limit) on the decreasing side. Practical values of the threshold values can be appropriately determined. For example, Thb=Thd=20(%) can be set in inequalities (1a) and (1b).

It is also possible to dynamically change the threshold values in accordance with the results of periodical blood pressure measurements using a cuff. For example, if the result of cuff blood pressure measurement is smaller than a predetermined value, it is possible to make the threshold value on the decreasing side stricter (make the threshold value easier to exceed) than when the measurement result is not smaller than the predetermined value, thereby monitoring the decrease in blood pressure more strictly. More specifically, when the normal range is defined by the upper and lower limits, the lower limit is set to be high. In this case, the lower limit becomes easier to exceed, so the decrease in blood pressure can be strictly monitored. On the contrary, if the cuff measurement result is large, it is possible to make the threshold value on the increasing side stricter (make the upper limit of the normal range smaller).

The fluctuation amount need not be a ratio (percentage), but may also be a difference.

If the fluctuation amount is found to be abnormal in step S115, the flow advances to step S130. If the fluctuation amount is found to be normal in step S115, the flow returns to step S111 to continue the processing for the next heart beat.

In steps S121 to S125, the same blood pressure estimating process as the conventional method is executed.

In step S121, the pulse wave propagation time is calculated on the basis of an ECG detected by the electrocardiogram electrode 20 and a plethysmograph sensed by the finger sensor 30. More specifically, the controller 100 performs signal processing such as noise removal and waveform shaping normally performed on an ECG and plethysmograph, and calculates the time difference between feature points in the heart beats of the ECG and plethysmograph as the pulse wave propagation velocity. In this case, the feature point of the ECG can be, e.g., the peak position of the R wave, and the feature point of the plethysmograph can be the leading edge of the waveform. Also, as described above, there is a time difference (preelection period) between the appearance of the R wave to the generation of the actual pulse wave. Therefore, correction can be performed by subtracting a time corresponding to a preejection period statistically calculated beforehand from the time difference between the feature points.

In step S123, an estimated blood pressure is obtained from the calculated pulse wave propagation time.

That is, an estimated blood pressure is calculated by applying the pulse wave propagation time to $$\text{Estimated blood pressure} = \alpha \times (\text{pulse wave propagation time [msec]}) + \beta \quad (2)$$

($\alpha$ and $\beta$ are coefficients, $\alpha<0$, $\beta>0$) as disclosed in, e.g., Japanese Patent Laid-Open No. 10-66681.

Note that the coefficients $\alpha$ and $\beta$ need only be determined in advance. That is, this equation is a linear equation with two unknowns, so the values of the coefficients $\alpha$ and $\beta$ can be determined by using at least two actually measured blood pressures and the corresponding pulse wave propagation times.

Each coefficient need not be fixed but may also be updated to an optimum value by using an actually measured value obtained by another method (cuff measurement or direct measurement) and the pulse wave propagation time at the corresponding timing.

In step S125, whether the estimated blood pressure is an abnormal value is determined. This determination can be performed by determining whether the estimated blood pressure is larger than the upper limit or smaller than the lower limit of a predetermined normal range, or determining whether the estimated blood pressure fluctuates more than a predetermined amount (which can be either a fluctuation ratio or difference) from the value of the last cuff blood pressure measurement.

Like the threshold values of the waveform parameters, these upper limit, lower limit, and fluctuation amount can be either fixed with respect to the value of cuff blood pressure measurement, or dynamically changed in accordance with practical measured values.

If the estimated blood pressure is found to be abnormal in step S125, the flow advances to step S130. If the estimated blood pressure is found to be normal in step S125, the flow returns to step S121 to continue the processing for the next heart beat.

In step S130, whether the conditions for executing cuff blood pressure measurement are satisfied is determined. That is, whether one of the following conditions is met is determined.

(1) Both the pulse wave parameter and estimated blood pressure are continuously found to be abnormal for a predetermined period.

(2) A predetermined time has elapsed since the last cuff blood pressure measurement.

If one of these conditions is met, the controller 100 controls the pump 14 to raise the pressure of the cuff 10, monitors the input signal from the pressure sensor 12 while gradually exhausting the air after avascularization, and calculates the highest blood pressure, average blood pressure, and lowest blood pressure on the basis of the well-known oscillometric method. The controller 100 also stores, in the storage unit 90, the waveform parameters and estimated blood pressure obtained immediately before the blood pressure measurement using the cuff 10, and uses them in calibration of the coefficients $\alpha$ and $\beta$ contained in the equation for calculating the estimated blood pressure and in processing after that. Note that during the cuff blood pressure measurement, the waveform parameter calculation and determination process in steps S111 to S115 and the estimated blood pressure calculation process in steps S121 to S125 are interrupted, or the results are ignored.

After that, the above processing is repeated until the termination of monitoring is designated.

Figure 4:
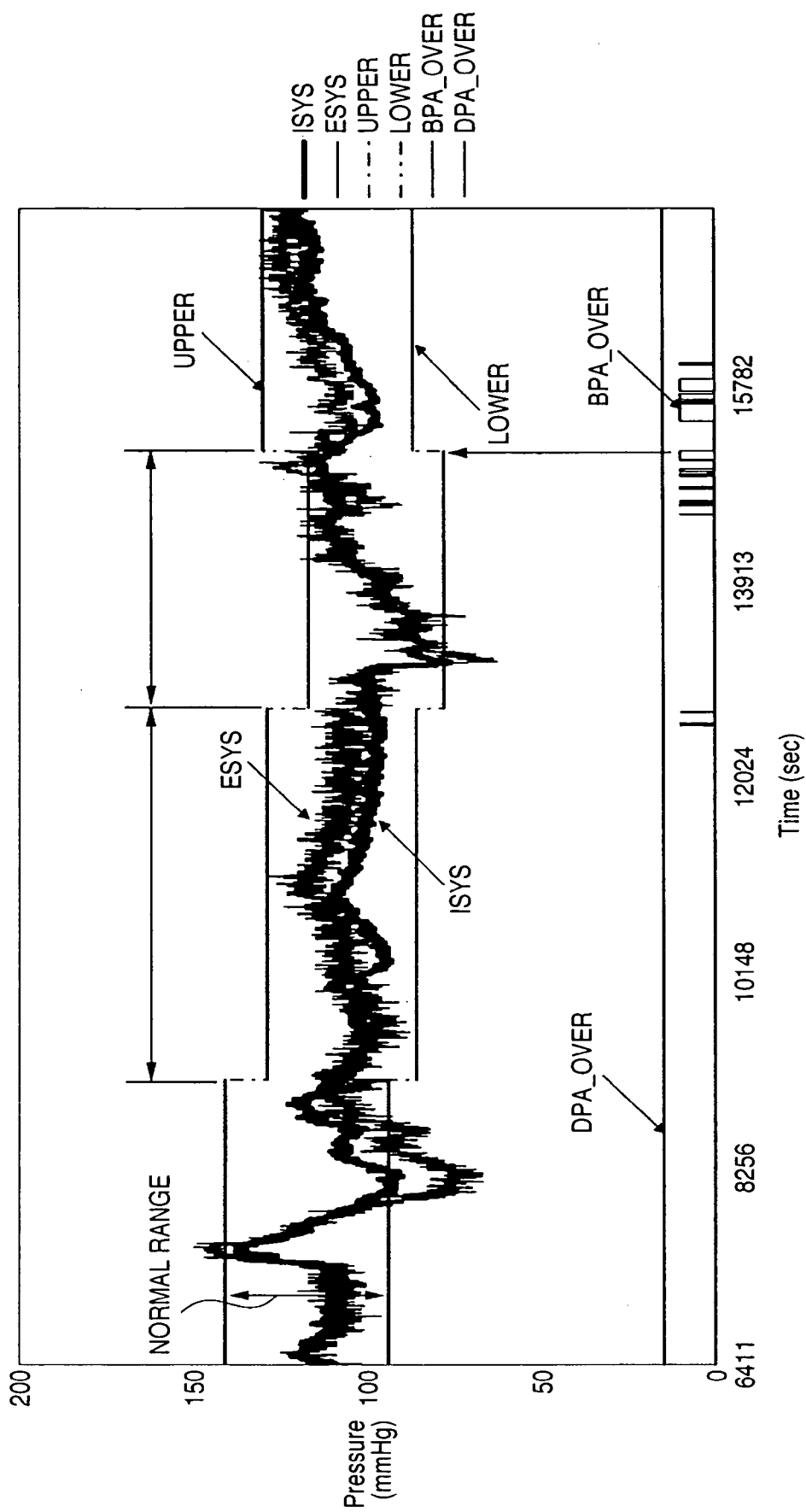
FIG. 4 is a graph showing actual examples of blood pressure calculated by the biological information monitoring apparatus according to the embodiment, a direct blood pressure measured invasively, and waveform parameters.

FIG. 4 is a graph showing the relationship between an estimated blood pressure continuously calculated by the blood pressure measuring apparatus of this embodiment, a direct blood pressure measured invasively, and waveform parameters.

Referring to FIG. 4, ESYS indicates the estimated blood pressure calculated on the basis of the pulse wave propagation time, and ISYS indicates the direct blood pressure measured invasively. The straight lines drawn above and below these blood pressures indicate values which are +20% and −20%, respectively, from cuff measurement values when cuff measurement is performed at times t0, t1, and t2.

That is, FIG. 4 shows the direct blood pressure measured invasively in order to show the relationship between the estimated blood pressure and the actual blood pressure, but no invasive measurement is performed by the actual blood pressure monitoring apparatus (if direct measurement is performed, blood pressure estimation itself has no meaning). In practice, cuff measurement is periodically performed, and, during a period in which no cuff blood pressure measurement is performed, monitoring is performed using the estimated blood pressure based on the pulse wave propagation time. FIG. 4 shows the case in which the last cuff blood pressure measurement values ±20% are used as the threshold values for determining whether the estimated blood pressure can be regarded as a normal value.

FIG. 4 also shows whether the waveform parameters b/a and d/a have exceeded the threshold values by BPA_OVER and DPA_OVER, respectively.

In FIG. 4, between times t0 and t1, the waveform parameter (b/a) sometimes indicates an abnormal value. However, no cuff activation is performed because the estimated blood pressure falls within the normal range, and periodic cuff blood pressure measurement is performed at time t1 after a predetermined time has elapsed since time t0.

After time t1, the estimated blood pressure exceeds the lower limit and upper limit in some periods, but both the two waveform parameters have normal values, so no cuff activation is performed either. After that, however, both the estimated blood pressure and the waveform parameter (b/a) show abnormal values, so cuff blood pressure measurement is executed at time t2. Since (t1−t0)>(t2−t1), the cuff activation at time t2 is shorter than the periodic interval.

After time t2, the waveform parameter shows an abnormal value for a while, but the estimated blood pressure falls within the normal range, so no cuff activation is performed.

As shown in FIG. 4, the blood pressure monitoring apparatus of this embodiment determines the presence/absence of the true fluctuation in blood pressure by using the values of the parameters obtained from the accelerated pulse wave and indicating the state of the blood vessel, in addition to the estimated blood pressure calculated on the basis of the pulse wave propagation time obtained from an ECG and pulse wave. Accordingly, the necessity of cuff blood pressure measurement can be determined more accurately than the conventional methods.

Equation Calibrating Process

The process of calibrating the equation for calculating the estimated blood pressure in the blood pressure monitoring apparatus of this embodiment will be explained below.

As described above, when the result of the cuff blood pressure measurement is periodically obtained, the equation for calculating the estimated blood pressure can be calibrated (the coefficients $\alpha$ and $\beta$ can be calibrated) on the basis of the measurement result. By this calibration, it is possible to increase the accuracy of the estimated blood pressure in an interval before the next cuff measurement. In this embodiment, the equation is calibrated on the basis of the result of the cuff blood pressure measurement, and calibration is performed by taking account of the fluctuation amounts of the waveform parameters of the accelerated pulse wave described above. As a consequence, the estimation accuracy can be increased.

As already described above, the equation for calculating the estimated blood pressure from the pulse wave propagation time can be represented by $$\text{Estimated blood pressure} = \alpha \times (\text{pulse wave propagation time [msec]}) + \beta \quad (2)$$

($\alpha$ and $\beta$ are coefficients, $\alpha<0$, $\beta>0$)

By calibrating each of these coefficients in accordance with the difference (error) between the actually measured value and the estimated value, or the difference between the last measured value and the present measured value, a more accurate estimated blood pressure can be calculated in processing after that.

In this embodiment, therefore, equation (2) is rewritten into $$\text{Estimated blood pressure} = (\alpha+\gamma) \times (\text{pulse wave propagation time [msec]}) + \beta \quad (2')$$

($\alpha$, $\beta$, and $\gamma$ are coefficients, $\alpha<0$, $\beta>0$)

thereby introducing a new coefficient $\gamma$. The coefficient $\gamma$ is a correction term of the coefficient $\alpha$, and has a value corresponding to the fluctuation amount of the waveform parameter obtained from the accelerated pulse wave. That is, if the fluctuation in waveform parameter of the accelerated pulse wave is large, the blood vessel may have functionally changed. Therefore, it is presumably favorable to make the degree of correction larger than that when the fluctuation in waveform parameter is small.

In this embodiment, the coefficient $\alpha$ is corrected as shown in, e.g., Table 1.

TABLE 1

| d | Correction amount of $\alpha$ |
|---|---|
| 30 < d | Recalculate |
| 20 < d ≦ 30 | +10 |
| 10 < d ≦ 20 | +5 |
| −10 ≦ d ≦ 10 | 0 (No correction) |
| −20 ≦ d < −10 | −5 |

TABLE 1-continued

| d | Correction amount of $\alpha$ |
|---|---|
| −30 ≦ d < −20 | −10 |
| d < −30 | Recalculate |

Note that d is (estimated blood pressure−actually measured value) or (actually measured value (t−1)−actually measured value (t)) [mmHg].

If d≧30 or d≦−30, it is determined that simple correction has no effect, so the coefficient is recalculated by using the present measured value and the last measured value.

The coefficient $\beta$ is also calibrated by using the calibrated coefficient $\alpha$ and the actually measured value.

The correction term $\gamma$ is introduced when the fluctuation amount (the difference absolute value or fluctuation ratio of the parameter value) of the waveform parameter from the value obtained by the last cuff blood pressure measurement exceeds a predetermined value. For example, when the fluctuation amount is D1(%) or D2(%) described above, it has values as shown in Table 2 below.

TABLE 2

| D (D1 and/or D2) | $\gamma$ |
|---|---|
| 30 < D | +3 |
| 20 < D ≦ 30 | +2 |
| 10 < D ≦ 20 | +1 |
| −10 ≦ D ≦ 10 | 0 |
| −20 ≦ D < −10 | −1 |
| −30 ≦ D < −20 | −2 |
| D < −30 | −3 |

Note that when a plurality of waveform parameters (b/a and d/a) are used as in this embodiment, it is possible to appropriately set the waveform parameter fluctuation amount on the basis of which $\gamma$ is to be introduced. For example, $\gamma$ is introduced if the fluctuation amount of one parameter exceeds the threshold value.

Note that in Table 2, the value of the correction amount $\gamma$ changes in accordance with the value of the waveform parameter fluctuation amount D. However, the value of the correction amount $\gamma$ may also be changed in accordance with the value of d. For example, as the value of d increases, the value of $\gamma$ is increased. It is also possible to combine these conditions, e.g., it is possible to add the value of $\gamma$ obtained by D and the value of $\gamma$ obtained by d. Alternatively, if the waveform parameter fluctuation amount D or d satisfies the condition of introducing the correction amount, the absolute value of $\gamma$ may also be held constant regardless of the value of D or d. More specifically, if 10<D in Table 2, $\gamma$ of +2 is unconditionally introduced, and, if D<−10 in Table 2, $\gamma$ of −2 is unconditionally introduced.

Figure 5:
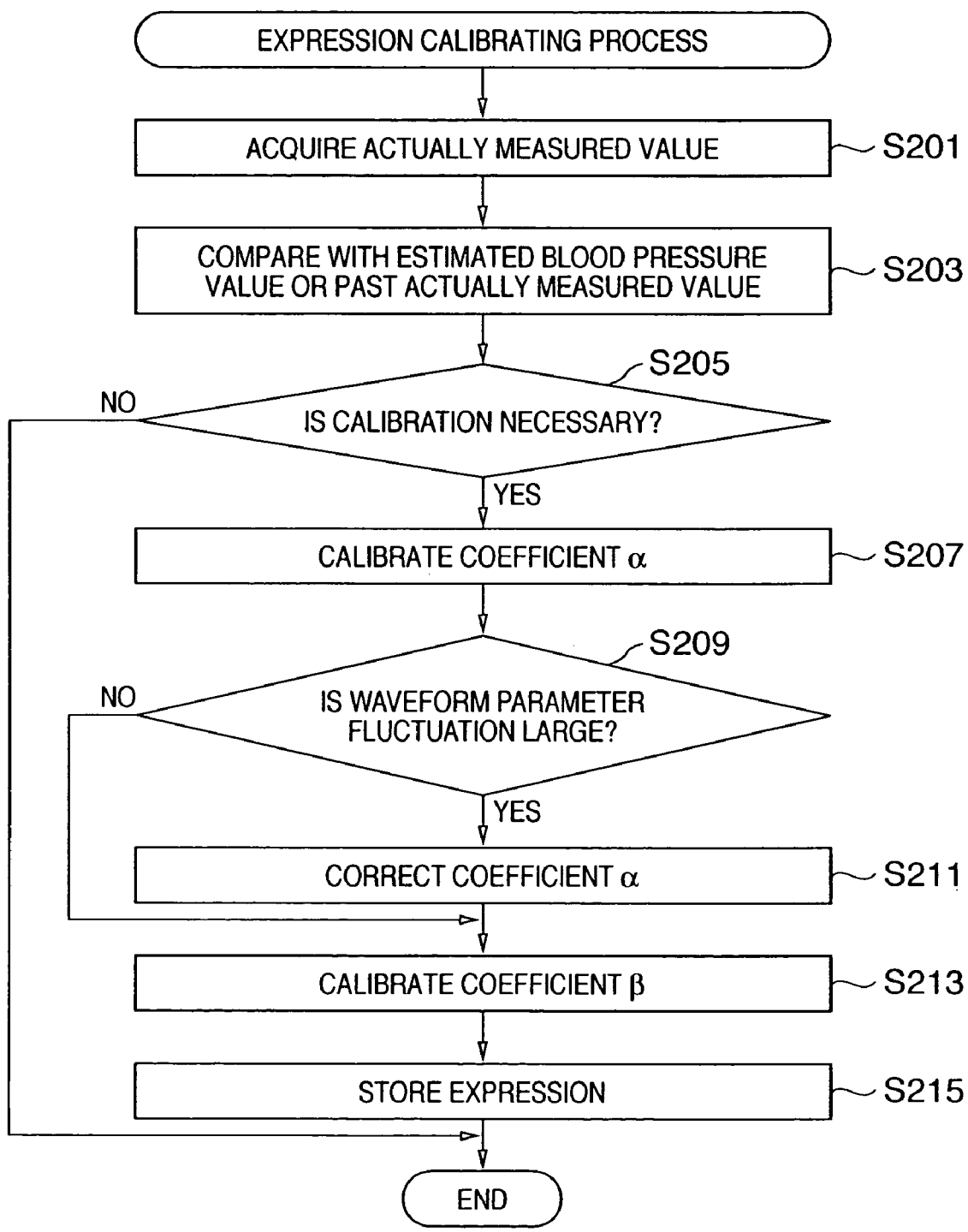
FIG. 5 is a flowchart explaining the operation of calibrating an expression for calculating an estimated blood pressure, in the biological information monitoring apparatus according to the embodiment of the present invention.

FIG. 5 is a flowchart for explaining the equation calibrating operation in the biological information monitoring apparatus of this embodiment. Similar to the blood pressure monitoring process described above, the following processing is implemented when the controller 100 executes the control program. It is also possible to perform the processing after step S140 is completed and before the flow returns to step S121 in the flowchart shown in FIG. 3.

First, in step S201, blood pressure (actually measured value) measured by using a cuff is acquired. In step S203, the actually measured value is compared with an estimated blood pressure obtained immediately before the cuff blood pressure measurement is started, or with an immediately preceding actually measured value. In step S205, on the basis of the difference or fluctuation ratio, whether the equation for calculating the estimated blood pressure need be calibrated is determined.

More specifically, as described above, it is determined that calibration is necessary if the fluctuation amount is large, on the basis of conditions such as (When determination is performed by the difference)

|Estimated blood pressure−actually measured value|>$Th1$

|Actually measured value $(t-1)$−actually measured value $(t)$|>$Th2$ (When determination is performed by fluctuation ratio)

|(Estimated blood pressure/actually measured value)−1|>$Th3$

|(Actually measured value $(t-1)$/actually measured value $(t)$)−1|>$Th4$

If it is determined that no calibration is necessary (the accuracy of the estimated blood pressure is satisfactory), the processing is terminated.

If it is determined that calibration is necessary, the coefficient is calibrated in step S207. As described above, the coefficient α is first calibrated in accordance with the value of d which is (estimated blood pressure−actually measured value) or (actually measured value (t−1)−actually measured value (t)).

Then, in step S209, whether it is necessary to perform correction taking account of the waveform parameter fluctuation amount, more specifically, whether the waveform parameter fluctuation amount is large, is determined on the basis of inequalities (1a) and (1b) described above. In this case, it is determined that the fluctuation amount is large if one parameter satisfies inequalities (1a) and (1b).

If the waveform parameter fluctuation is found to be large, the coefficient α is corrected by γ described above in step S211. In step S213, the coefficient β is corrected by using the calibrated coefficient α (if the waveform parameter fluctuation is not large) or the calibrated and corrected coefficient α (if the waveform parameter fluctuation is large) and the actually measured blood pressure. The calibrated coefficients or the expression containing the calibrated coefficients is stored in the storage unit 90.

In this embodiment as described above, in the blood pressure monitoring apparatus which calibrates the expression for calculating the estimated blood pressure from the pulse wave propagation velocity during blood pressure measurement using a cuff, the calibration amounts of coefficients are corrected if the waveform parameter fluctuation amount obtained from the accelerated pulse wave is large. Accordingly, accurate calibration can be performed even if the functionality of the blood vessel changes, e.g., even if the blood vessel abruptly expands or contracts. As a consequence, an accurately estimated blood pressure can be obtained.

Note that in the above embodiment, the pulse wave propagation velocity is measured by using an ECG and plethysmograph in order to use an ordinary biological information monitoring apparatus. However, the present invention is also applicable to blood pressure monitoring apparatus which calculates the pulse wave propagation velocity by another method. For example, the present invention is applicable to an apparatus which measures the pulse wave propagation time from a pulse wave measured by a cuff which is pressurized to a diastolic pressure or less and a plethysmograph, and an apparatus which measures the pulse wave propagation time from a pulse wave sensed by a pulse wave sensor and a pulse wave sensed by a cuff.

In addition, in the above embodiment, the method using the blood pressure measured by the oscillometric method using a cuff is explained as a method of measuring the blood pressure in accordance with the result of determination using the estimated blood pressure and accelerated pulse wave parameters, and measuring the blood pressure to be used to calibrate the coefficients. However, the result of determination obtained by the present invention by using the estimated blood pressure and accelerated pulse wave parameters may also be used to determine whether to perform blood pressure measurement using another arbitrary blood pressure measuring method including a method of capable of continuous blood pressure measurement. Furthermore, as the blood pressure to be used to calibrate the coefficients of the expression for calculating the estimated blood pressure, it is possible to use blood pressure measured by using another arbitrary blood pressure measuring method, provided that the value has accuracy to such an extent that it can be used as the reference of calibration.

As many apparently widely different embodiments of the present invention can be made without departing from the spirit and scope thereof, it is to be understood that the invention is not limited to the specific embodiments thereof except as defined in the appended claims.

What is claimed is:

1. Blood pressure monitoring apparatus comprising:
   blood pressure measuring unit adapted to measure blood pressure in response to blood pressure measurement designation;
   pulse wave acquiring unit adapted to acquire a pulse wave in a predetermined location of a living body;
   pulse wave propagation time calculating unit adapted to calculate a pulse wave propagation time from the pulse wave, and one of an electrocardiogram and a pulse wave acquired from a location different from the predetermined location;
   estimated blood pressure calculating unit adapted to calculate an estimated blood pressure on the basis of the pulse wave propagation time;
   accelerated pulse wave calculating unit adapted to calculate an accelerated pulse wave from the pulse wave;
   waveform parameter calculating unit adapted to calculate a predetermined waveform parameter from a waveform contained in the accelerated pulse wave; and
   control unit adapted to provide the blood pressure measurement designation to said blood pressure measuring unit to cause said blood pressure measuring unit to measure blood pressure, if both the estimated blood pressure and the predetermined waveform parameter are abnormal.

2. The apparatus according to claim 1, wherein the predetermined waveform parameter comprises at least one of a parameter concerning a presystolic component, and a parameter concerning a telesystolic component.

3. The apparatus according to claim 2, wherein the predetermined waveform parameter comprises a wave height ratio of characteristic waveforms contained in the accelerated pulse wave.

4. The apparatus according to claim 3, wherein the predetermined waveform parameter comprises a wave height ratio of b-wave to a-wave contained in the accelerated pulse wave, and a wave height ratio of d-wave to a-wave contained in the accelerated pulse wave.

5. The apparatus according to claim 1, wherein said control unit causes said blood pressure measuring unit to measure blood pressure whenever a predetermined time has elapsed, regardless of the estimated blood pressure and a value of the predetermined waveform parameter.

6. The apparatus according to claim 1, wherein said control unit determines whether the predetermined parameter is abnormal by comparing a value of the predetermined parameter with a predetermined normal range, and wherein the predetermined normal range is determined in accordance with blood pressure measured last by said blood pressure measuring unit.

7. The apparatus according to claim 6, wherein a lower limit which defines the normal range is set higher when the blood pressure measured last by said blood pressure measuring unit is not more than a predetermined value, than when the blood pressure is larger than the predetermined value.

8. The apparatus according to claim 1, wherein said blood pressure measuring unit measures blood pressure by a method incapable of continuous measurement.

9. The apparatus according to claim 1, wherein said blood pressure measuring unit measures blood pressure by an oscillometric method using a cuff.

10. The apparatus according to claim 1, wherein said pulse wave acquiring unit acquires a plethysmograph.

11. The apparatus according to claim 1, wherein the accelerated pulse wave is obtained by calculating a second derivative of a pulse wave.

12. Blood pressure monitoring apparatus comprising:
blood pressure measuring unit adapted to measure blood pressure by a predetermined method;
pulse wave acquiring unit adapted to acquire a pulse wave in a predetermined location of a living body;
pulse wave propagation time calculating unit adapted to calculate a pulse wave propagation time from the pulse wave, and one of an electrocardiogram and a pulse wave acquired from a location different from the predetermined location;
estimated blood pressure calculating unit adapted to calculate an estimated blood pressure by applying the pulse wave propagation time to a predetermined expression;
accelerated pulse wave calculating unit adapted to calculate an accelerated pulse wave from the pulse wave;
waveform parameter calculating unit adapted to calculate a predetermined waveform parameter from a waveform contained in the accelerated pulse wave; and
calibrating unit adapted to calibrate the expression by using a value measured by said blood pressure measuring unit,
wherein if a fluctuation amount of the waveform parameter exceeds a predetermined amount, said calibrating unit performs the calibration after correcting a calibration amount which is applied when the fluctuation amount of the waveform parameter does not exceed the predetermined amount.

13. The apparatus according to claim 12, wherein the correction is performed by applying a calibration amount larger than the calibration amount applied when the fluctuation amount of the waveform parameter does not exceed the predetermined amount.

14. The apparatus according to claim 12, wherein said calibrating unit determines whether to perform the calibration on the basis of one of a comparison of a present measured value and a last measured value obtained by said blood pressure measuring unit, and a comparison of the present measured value obtained by said blood pressure measuring unit and the estimated blood pressure, and performs the calibration only when determining that the calibration is necessary.

15. The apparatus according to claim 12, wherein a degree of the correction is constant.

16. The apparatus according to claim 12, wherein a degree of the correction changes in accordance with one of the fluctuation amount of the waveform parameter, a result of a comparison of a present measured value and a last measured value obtained by said blood pressure measuring unit, and a result of a comparison of the present measured value obtained by said blood pressure measuring unit and the estimated blood pressure.

17. The apparatus according to claim 12, wherein the expression is represented by
Estimated blood pressure $=\alpha \times$(pulse wave propagation time [msec])$+\beta$ ($\alpha$ and $\beta$ are coefficients, $\alpha<0$, $\beta>0$), and wherein said calibrating unit calibrates the expression by applying the calibration amount to the coefficient $\alpha$, and calibrating the coefficient $\beta$ by applying, as the estimated blood pressure, a measured value obtained by said blood pressure measuring unit.

18. The apparatus according to claim 17, wherein if the fluctuation amount of the waveform parameter exceeds the predetermined value, said calibrating unit corrects the calibration amount of the coefficient $\alpha$.

19. The apparatus according to claim 12, wherein the predetermined waveform parameter comprises at least one of a parameter concerning a presystolic component, and a parameter concerning a telesystolic component.

20. The apparatus according to claim 19, wherein the predetermined waveform parameter comprises a wave height ratio of characteristic waveforms contained in the accelerated pulse wave.

21. The apparatus according to claim 20, wherein the predetermined waveform parameter comprises a wave height ratio of b-wave to a-wave contained in the accelerated pulse wave, and a wave height ratio of d-wave to a-wave contained in the accelerated pulse wave.

22. The apparatus according to claim 12, wherein said blood pressure measuring unit measures blood pressure by a method incapable of continuous measurement.

23. The apparatus according to claim 12, wherein said blood pressure measuring unit measures blood pressure by an oscillometric method using a cuff.

24. The apparatus according to claim 12, wherein said pulse wave acquiring unit acquires a plethysmograph.

25. The apparatus according to claim 12, wherein the accelerated pulse wave is obtained by calculating a second derivative of a pulse wave.

* * * * *